US00PP13617P2

(12) United States Plant Patent
Vardi et al.

(10) Patent No.: US PP13,617 P2
(45) Date of Patent: Mar. 4, 2003

(54) CITRUS TREE NAMED 'VERED'

(75) Inventors: Aliza Vardi, Ramat Gan (IL); Pinchas Spiegel-Roy, Ramat-Gan (IL); Ahuva Frydman-Shani, Ramat-Gan (IL); Avraham Elchanati, Holon (IL); Hana Neumann, Hemed (IL)

(73) Assignee: State of Israel-Ministry of Agriculture and Rural Development, Tel Aviv (IL)

( * ) Notice: Subject to any disclaimer, the term of this patent is extended or adjusted under 35 U.S.C. 154(b) by 0 days.

(21) Appl. No.: 09/716,983

(22) Filed: Nov. 20, 2000

(51) Int. Cl.[7] ..... A01H 5/00
(52) U.S. Cl. ..... Plt./202

(58) Field of Search ..... Plt./202

(56) References Cited

PUBLICATIONS

GTITM UPOV ROM Citation For 'Vered' As Per Il PBR02642; Feb. 26, 1999.*

* cited by examiner

*Primary Examiner*—Kent L. Bell
(74) *Attorney, Agent, or Firm*—Akerman Senterfitt

(57) ABSTRACT

A new variety of mandarin citrus is described that is distinguished by fruit having a reddish-orange color, few seeds, and large size.

2 Drawing Sheets

FIELD OF THE INVENTION

A new mandarin citrus tree *Citrus reticulata* is described. The new variety is designated 'Vered' and is desirable to the consumer because of the red-orange color of the fruit, and relatively large size. The fruit is seedless or has only a few seeds when exposed to cross-pollination.

BACKGROUND OF THE NEW PLANT

The present invention relates to a new and distinct variety of mandarin citrus tree of the genus *Citrus reticulata* hybrid developed by inventors Aliza Vardi, Pinchas Spiegel-Roy, Avraham Elchanati, Ahuva Frydman-Shani and Hana Neumann in Bet Dagan, Israel from a controlled pollination cross between a seedless parent 'Satsuma' (unpatented) mandarin and pollen parent 'Michal' (unpatented).

Asexual reproduction by conventional bud grafting of the new variety at the Agriculture Research Organization Volcani Center in Bet Dagan, Israel, has shown that the new characteristics are stabilized and permanently fixed through successive propagation.

The objective in breeding the present new tree variety, assigned the denomination 'Vered', was to obtain citrus mandrins with few or no seeds. In the spring of 1982, a controlled pollination cross between 'Satsuma' mandarin (*Citrus unshiuma c.*) as seed parent and pollen parent 'Michal', a cultivar of Israeli origin believed to be a natural hybrid between two *Citrus reticulata* Blanco cultivars was made at the Agricultural Research Organization, The Volcani Center, Bet Dagan, Israel. The fruit was collected in November 1982. Seeds were extracted and germinated in January 1983. About 200 seedlings were grown from the germinated seeds. The zygotic seedlings were isolated and each grafted onto Troyer rootstock The grafted plants were grown in an insect proof screen house. The procedure employed inducing root restriction, lateral shoot removal, limb bending and optimum irrigation, known as drip irrigation combined with liquid fertilization, resulting in an apparent reduction in the length of the juvenile period and eliminating the chances of cross pollination.

The first fruits were observed in November–December, 1987 and again in 1988. One of 60 scions was designated 21/8/3. This scion was observed to be fully ripe in the last week of December to the end of January. The fruit of this selection was orange-red in color and completely seedless.

Bud wood was taken from 21/8/3 and grafted in the spring of 1988 on 6 Troyer rootstocks. The grafted plants were planted a year later in the experimental grove of the Agricultural Research Organization, Bet Dagan, Israel. The first crop of these trees was obtained in 1993. The yield of the scion grafted onto Troyer rootstock was good. The fruit was fully ripe in the last week of December. The color of the fruit when fully ripe was orange-red, and the fruit was quite easy to peel. The fully ripe fruit had a very pleasant flavor and the juice had a sugar concentration of about 14.3% and an acid concentration of about 1.4%.

SUMMARY OF THE INVENTION

21/8/3, designated 'Vered', is characterized by a seedless fruit as having seedless fruit or fruit having only a few seeds when exposed to cross-pollination. There are few flowers with anthers bearing semi-fertile pollen (54% acetocarmine stained pollen. Table 1 shows some of the characteristics of 'Vered' compared with the seed parent 'Satsuma' mandarin and pollen parent 'Michal'.

Color designations have been determined from the RHS Colour Chart published by The Royal Horticultural Society, London.

TABLE 1

| Tree | Pollen fertility[1] | Flower size | Seeds/fruit | Rind |
|---|---|---|---|---|
| 21/8/3 'Vered' | 54% | | 0–9 | Smooth, red-orange RHS 34A |

TABLE 1-continued

| Tree | Pollen fertility[1] | Flower size | Seeds/fruit | Rind |
|---|---|---|---|---|
| 'Satsuma' mandarin | 10–30% | | 0–6 | |
| 'Michal' | 86% | | 2–9 | Smooth,deep red-orange RHS 33A |

[1]Estimated by acetocarmine staining

The following is a detailed description of the new mandarin citrus variety based on observations made under typical Israeli grove conditions when the citrus was 5–6 years old.

The leaf shape, tree size and shape somewhat resemble 'Satsuma' mandarin. Young shoots have no anthocyanin coloration at the tip.

The tree is quite productive with a slight tendency to alternate bearing (less fruit is borne the following year if a heavy crop is not harvested). The canopy is moderately dense. The bark of the young shoots is initially smooth and green gradually turning into a smooth greyed-green color.

The chromosome number of the tree is diploid (2n=18) as is the chromosome number of the parents.

The leaves are similar to those of 'Satsuma' in shape and size. Foliar flushes, as measured in Bet Dagan, Israel, occur between April and September. The color and veination of the leaves are similar to 'Satsuma'. Leaf blade is firm, without undulation and straight in cross section. Petioles are without wings or have rudimentary wings.

The characteristics of flowering and flower parts are different from both parents. The flower is bigger than the flower of 'Michal' and almost the same size as the flower of 'Satsuma' with longer anthers which reach the stigma. Flowering as measured in Bet Dagan, Israel occurs between mid March and the beginning of April. Terminal flower buds have no anthocyanin coloration. Anther color is yellow with 54% stainable pollen grain as stained with acetocarmine.

The fruit has few seeds, about 0–9 seeds per fruit. The fruit shape is somewhat flat and is medium to large in size. When 50 fruits were measured, the fruit had an average weight 210 grams, an average height 63 mm, and an average diameter 79 mm. The fruit surface is usually smooth with a reddish-orange color and bears an average number of conspicuous rind oil glands. Fruit ripening does not differ from outside of the canopy to the inside, but the fruit color of the outside canopy is a little brighter as compared to the fruit color of the inside canopy. There is no persistence of the style and the areola is not completely developed. A naval is absent or very rare. The rind is thin and relatively easy to peel.

The color of the albedo is white and the flesh is dark orange in color. The fruit contain 10–11 segments and is very juicy. The external color of the seeds is white, becoming pale brown when dry. The color of the cotyledons is green.

Polyembryonic seeds are present. The seed size, shape and texture are quite similar to Satsuma. The fruit reaches maturity in January in Israel. The ripening of the fruit on the tree and within the fruit is uniform. Fruit remaining on the tree does not regreen and begins to lose quality in mid February.

DESCRIPTION OF THE PHOTOGRAPHS

The new citrus tree is illustrated in the accompanying color photographs.

Sheet one depicts the whole tree and canopy shape of the new variety.

Sheet two shows the exterior of the fruit as well as transverse midsections in a plane substantially perpendicular to the axis, illustrating the interior of the fruit.

DESCRIPTION OF THE NEW TREE

The following is a detailed description of the new mandarin citrus variety 'Vered' based on observations made under typical Israeli grove conditions.

Tree:

*Origin.*—Cross between seed parent 'Satsuma' mandarin and pollen parent 'Michal'.

*Classification.*—Botanical: *Citrus reticulata* hybrid. Common: Mandarin citrus. Cultivar: 'Vered'.

*Shape.*—Upright, somewhat spreading.

*Thorns.*—The fruit bearing branches are thornless.

*Branching.*—Upright.

*Canopy.*—Moderately dense.

*Bark.*—Immature: Smooth, green, RHS 137B. Mature: Smooth, greyed-green, RHS 197A.

*Height.*—2.5–3 m.

*Width.*—3–3.5 m.

*Productivity.*—60 kg per tree each season.

*Leaf.*—Size: Length 100 mm, width: 49 mm. Shape: Large, long, lanceolate and tapering at base and apex. Leaf blade: Firm, without undulation, straight cross section. Petioles: Wingless 18 mm length, 2 mm in diameter, Green RHS 146B. Color: Upper: Green RHS 146A; lower: Green RHS 146B. Foliar flushes: April–September.

*Habit.*—Moderately vigorous.

*Disease resistance.*—No particular susceptibility or resistance observed.

Trunk diameter: 10 cm at 20 cm above the ground.

*Winter hardiness.*—Winter temperature in Bet Dagan, Israel averages 4–7 degrees Centigrade.

Flower:

*Petals.*—5.

*Petal color.*—White RHS 155B.

*Sepals.*—5.

*Anthers.*—20.

*Flowering period.*—Mid March to early April (Israel).

*Flower drop.*—April.

*Stamens.*—Approximately 20.

*Anther color.*—Yellow-orange RHS 18B.

*Pollen fertility.*—Fertile, 54% stainable pollen (acetocarmine stained).

*Anthocyanin coloration.*—No coloration.

Fruit:

*Shape.*—Subglobose.

*Size.*—Medium to large.

*Weight.*—210 g (average of 50 fruits).

*Height.*—63 mm.

*Diameter.*—79 mm.

*Surface color.*—Red-orange, RHS 34A.

*Rind oil gland.*—Conspicuous, average number.

*Style.*—No persistence.

*Navel.*—Absent.

*Rind.*—Thin and easy to peel.

*Albedo.*—Green-white RHS 157D.

*Areola*.—Incompletely developed.

*Fruit segments*.—10–11.

*Color of flesh*.—Dark orange.

*Time of maturity*.—Picking is from late December through January (Israel).

*Fruit extract*.—Quality tested Jan. 10, 1994. Total soluble solids (TSS): 14.3%. Acid content: 1.4%. TSS/acid ratio: 10.16.

Seeds:

*Number per fruit*.—0–9.

*Size*.—10 mm length, 6 mm width.

*Color*.—External: Yellow (fresh). Internal: Pale brown (dry).

*Cotyledons*.—Green.

*Embryony*.—Polyembryonic.

The tree and its fruit as described herein may vary somewhat in certain characteristics due to climate and/or soil conditions under which the variety is grown.

What is claimed is:

1. A new and distinct variety of *Citrus reticulata* tree substantially as herein described and shown.

* * * * *

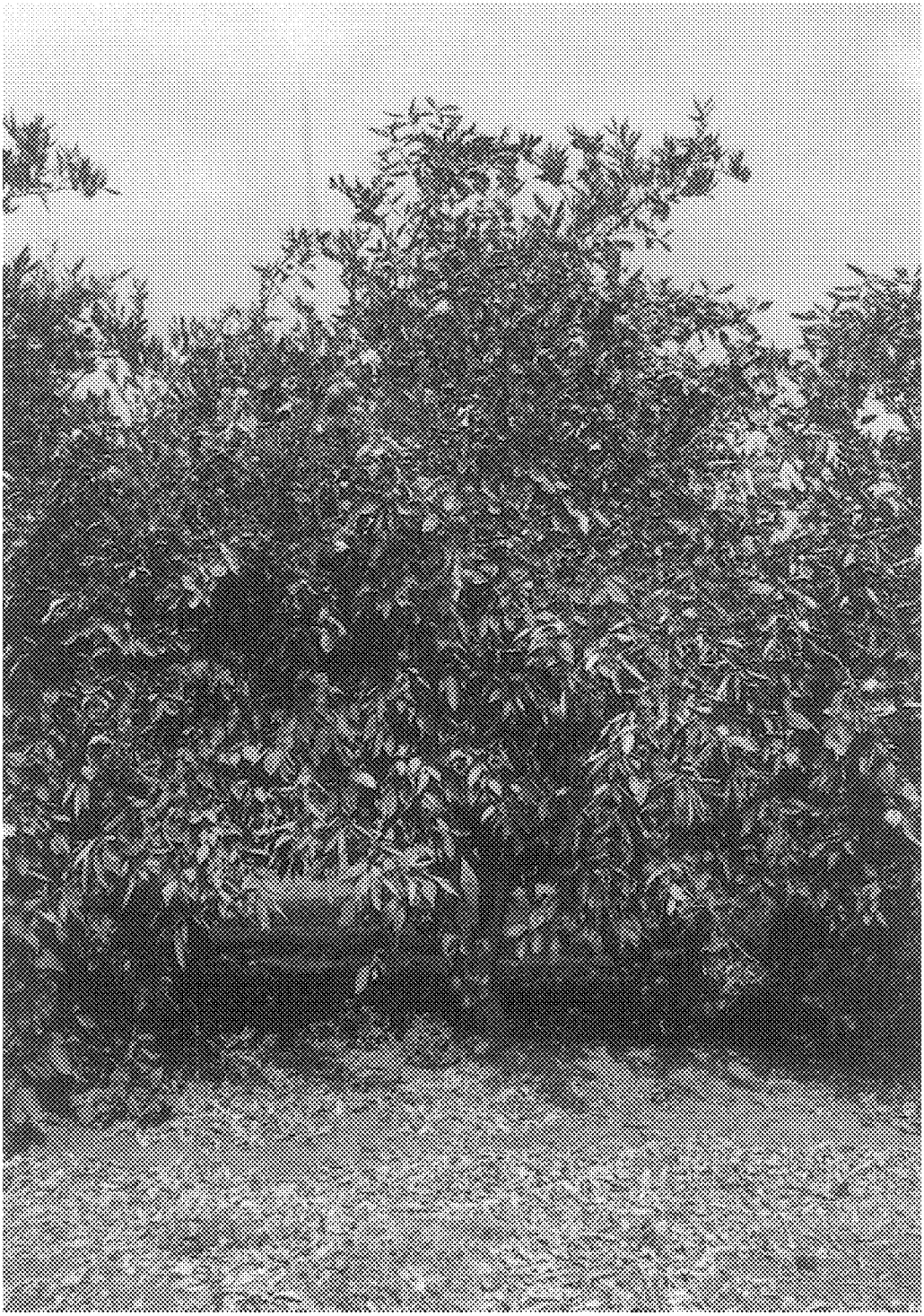

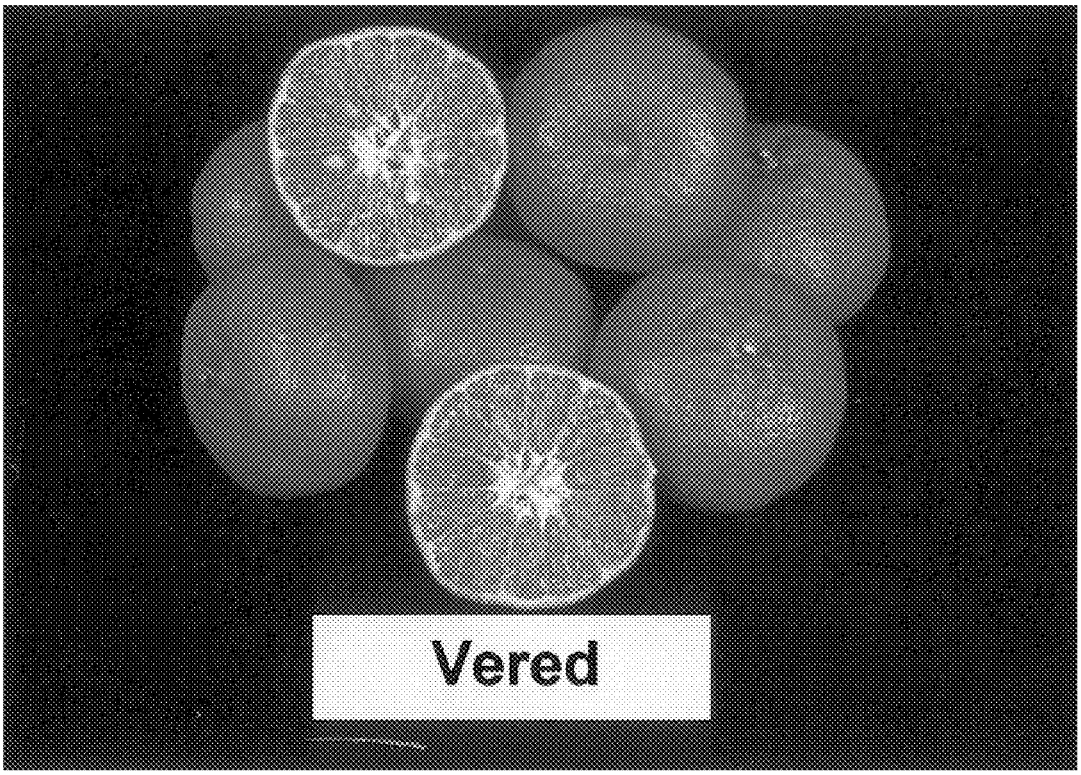
Vered